United States Patent [19]

Schmid et al.

[11] 4,001,254
[45] Jan. 4, 1977

[54] ISOTHIOCYANOPYRIDINE DERIVATIVES

[75] Inventors: Wolfgang Schmid, Therwil; Ernst Gutzwiller, Rheinfelden; Urs Meyer, Riehen, all of Switzerland

[73] Assignee: Ciba-Geigy Corporation, Ardsley, N.Y.

[22] Filed: Oct. 10, 1975

[21] Appl. No.: 621,443

Related U.S. Application Data

[62] Division of Ser. No. 386,796, Aug. 8, 1973, Pat. No. 3,929,806.

[30] Foreign Application Priority Data

Aug. 10, 1972 Switzerland ............... 11886/72
Aug. 10, 1972 Switzerland ............... 11887/72

[52] U.S. Cl. ............ 260/294.8 E; 260/294.8 G; 424/263
[51] Int. Cl.² ..................... C07D 213/74
[58] Field of Search ............ 260/294.8 E

[56] References Cited
UNITED STATES PATENTS 3,835,145  9/1974  Dickinson et al. ......... 260/294.8 E

*Primary Examiner*—Alan L. Rotman
*Attorney, Agent, or Firm*—Harry Falber

[57] ABSTRACT

New isothiocyanopyridines of the formula

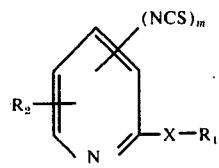

wherein $R_1$ represents hydrogen, alkyl, substituted alkyl, cycloalkyl, Cycloalkenyl, or a group of the formula

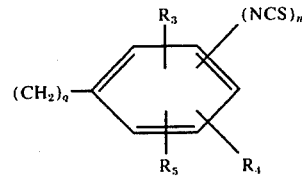

wherein $R_3$, $R_4$ and $R_5$ stand for hydrogen, alkyl, phenyl, benzyl, dialkylamino, alkoxycarbonyl, mono- or dialkylcarbamoyl, alkanoyl, halogen, nitro, alkoxy, alkylthio, halogenalkyl, cyano, hydroxy, aryloxy, arylthio, arylamino, aralkoxy, aralkylthio or aralkylamino, q represents 0 to 6, X represents oxygen, sulphur, sulphonyl or the group

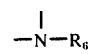

wherein
$R_6$ stands for hydrogen, alkyl, alkenyl, dialkylaminoalkyl, alkoxycarbonyl, alkanoyl, or together with the nitrogen atom and the substituent $R_1$ it represents a saturated or unsaturated heterocycle, which can further contain oxygen, sulphur, nitrogen or the group N-$R_7$, wherein $R_7$ represents hydrogen, methyl or ethyl, $R_2$ represents hydrogen or halogen, and in each case one of the symbols *m* and *n* denotes 1 while the other is 0, and their acid addition salts and quaternary salts non toxic to warm-blooded animals.

5 Claims, No Drawings

ISOTHIOCYANOPYRIDINE DERIVATIVES

This is a division of application Ser. No. 386,796, filed on Aug. 8, 1973, now U.S. Pat. No. 3,929,806.

The present invention relates to isothiocyanopyridines, to processes for the preparation of these new compounds, to anthelminthic agents, as well as to agents for defoliation and desiccation which contain these compounds as active substance.

Among the endoparasites occurring in warm-blooded animals, the helminths in particular do great harm. For example, animals infested with worms suffer not only inhibited growth but also, in some cases, such severe injury that the animals die. It is therefore of great importance that agents be developed which are suitable for the control of helminths and of their development stages, as well as for the prevention of infestation by these parasites. The term "helminths" in the present description covers nematodes, cestodes and trematodes, that is, worms of the gastrointestinal tract, of the liver and of other organs. A number of substances having an anthelmintic action have become known, but these are frequently not able to fully satisfy requirements: they may be insufficiently effective in compatible doses, or produce in therapeutically effective doses undesirable side effects, or have much too narrow a range of action. Thus, for example, racemic 2,3,5,6-tetrahydro-6-phenyl-imidazo(2,1-5)thiazole, known from the Dutch Patent Specification No. 6,505,806, is effective only against nematodes, but not against trematodes and cestodes.

The new isothiocyanopyridines correspond to formula I

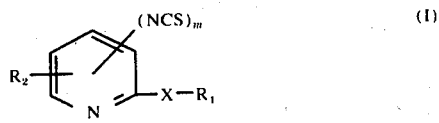

wherein $R_1$ represents hydrogen, a straight-chain or branched alkyl or alkenyl radical having 1 to 17 carbon atoms, which can be substituted by halogen, hydroxyl, lower alkoxy, phenoxy, lower alkylthio, lower alkylamino, di-lower alkylamino, cycloalkyl lower alkylamino, alkanoyl having 1 to 6 carbon atoms, or by a benzoyl radical optionally substituted by lower alkyl, halogen, trifluoromethyl or nitro, a mono-, bi- or tricyclic cycloalkyl or cycloalkenyl radical having 3 to 10 carbon atoms in the ring structure, optionally mono- or disubstituted by lower alkyl, whereby bi- and tricyclic radicals can be bound also by way of a methylene group to the group X, or a radical of the formula

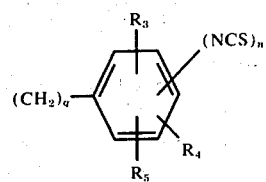

wherein $R_3$, $R_4$ and $R_5$ stand for hydrogen, straight-chain or branched alkyl having at most 5 carbon atoms, phenyl, benzyl, dialkylamino having a maximum of 4 carbon atoms, alkoxycarbonyl, mono- or dialkylcarbamoyl having 2–6 carbon atoms, alkanoyl having 2–5 carbon atoms, halogen, nitro, alkoxy or alkylthio having at most 4 carbon atoms, haloalkyl, cyano, hydroxy, optionally substituted aryloxy, arylthio or arylamino, or optionally substituted aralkoxy, aralkylthio or aralkylamino having at most 3 carbon atoms in the alkyl chain, $q$ represents 0 to 6, $x$ represents oxygen, sulphur, sulphonyl (—$SO_2$—) or the group

wherein $R_6$ stands for hydrogen, an alkyl or alkenyl radical having 1 to 15 carbon atoms, a dimethylamino or diethylamino-lower-alkyl radical, a lower alkoxycarbonyl radical, a lower-alkanoyl radical, or together with the nitrogen atom and the substituent $R_1$ it represents a saturated or unsaturated heterocycle having 4 to 6 carbon atoms, which can further contain oxygen, sulphur, nitrogen or the group N-$R_7$, wherein $R_7$ represents hydrogen, methyl or ethyl, $R_2$ represents hydrogen or halogen, and in each case one of the symbols $m$ and $n$ denotes 1 while the other is 0, and include the acid addition salts and quaternary salts non-toxic to warm-blooded animals.

The following may be mentioned as examples of straight-chain or branched alkyl radicals having up to 17 carbon atoms: methyl, ethyl, n-propyl, isopropyl, n-butyl, sec.butyl, isobutyl, tert.-butyl, n-amyl, isoamyl, hexyl, 1-ethylpentyl, octyl, undecyl, dodecyl, pentadecyl or heptadecyl.

Examples of straight-chain or branched alkenyl radicals are n-propenyl, α-methylvinyl, 9-decenyl or 8-heptadecenyl. The term 'lower alkyl' denotes a straight-chain or branched alkyl radical having 1 to 6, preferably 1 to 4, carbon atoms, The meaning of cycloalkyl or cycloalkenyl radicals includes also ring structures which can be substituted by methyl, ethyl, n-propyl or isopropyl. Given as examples are cyclopropyl, cyclobutyl, cyclopentyl, cyclohexyl, cyclohexenyl, 3,4-dimethylcyclobutyl, 2,3-dimethylcyclopropyl, 4-methylcyclohexyl, 4-isopropylcyclohexyl, 3,5-bis-(ethyl)cyclohexyl, norbornyl, norbornylmethyl and adamantyl.

The term 'halogen' embraces fluorine, chlorine and bromine.

Saturated or unsaturated heterocycles formed from the substituents $R_1$ and $R_6$ together with the N-atom bound to them are, for example, pyrrolidine, piperidine, 2-methylpiperidine, 4-methylpiperidine, piperazine, N'-methyl- and N'-ethylpiperazine, morpholine, isomorpholine, thiomorpholine, hexamethyleneimine, pyrrole, indole, imidazole, imidazoline, pyrazole and pyrazoline.

The position of the substituents on the pyridine ring is to be so arranged that the substituent bound by way of the bridge-member X takes the position 2 or 4, and the NCS-group the position 3 or 5.

Suitable salts of the isothiocyanopyridines, non-toxic to warm-blooded animals, are addition compounds with inorganic or organic acids, preferably relatively strong acids, e.g.: hydrochloric acid, hydrobromic acid, sulphuric acid, phosphoric acid, acetic acid, adipic acid, maleic acid, tartaric acid, lactic acid, citric acid, glutamic acid, aconitic acid, sulphamic acid, methanesulphonic acid and p-toluenesulphonic acid. Where the basicity of the substituents on the pyridine ring permit it, salts may also be formed with weaker, preferably organic acids.

It is also possible to use quaternary salts obtained on the pyridine ring or on the substituent by reaction with alkylating agents such as, e.g. alkyl halides or sulphuric acid alkyl esters.

The compounds of formula I are highly effective against helminths, and can also be employed for defoliation and desiccation of unlignified parts of plants above the soil. The active substances are particularly suitable for defoliation and desiccation of cotton plants, leguminosae, sorghum, soya beans, potatoes and grape vines before the harvest, without impairment of subsequent ripening. Furthermore, these active substances may be used also for the treatment of plants such as ornamental plants (chrysanthemums, roses) or tree-nursery material (ornamental shrubs and trees) which are to be transported, as well as for the treatment of plant material intended for seed production.

To be especially emphasised are the compounds of formula I wherein the isothiocyano group is in the 3- or 5-position, $R_1$ represents a straight-chain or branched alkyl radical having 1 to 10 carbon atoms, the cyclopropyl, cyclopropylmethyl, cyclobutyl, cyclopentyl or the cyclohexyl radical $R_2$ represents hydrogen, and $R_6$ hydrogen, a straight-chain or branched alkyl or alkenyl radical having 1 to 10 carbon atoms, or together with the nitrogen atom and $R_1$ represents a saturated or unsaturated heterocycle having 4 to 6 carbon atoms, which can contain, as a further hetero atom, also oxygen sulphur or nitrogen or the group

wherein $R_7$ stands for methyl or ethyl.

By virtue of their good biological activity, particularly important sub-groups of the active substances according to the invention are as follows:
— pyridine derivatives of the general formula I wherein the NCS-group forms a substituent of the pyridine ring, especially such derivatives
— in which the NCS-group occupies position 5 of the pyridine ring;
— pyridine derivatives wherein the NCS-group occupies position 5, the substituent bound by way of X position 2;
— pyridine derivatives wherein the NCS-group is in position 5, and the substituent bound by way of X in position 2, and in which one of the radicals $R_3$ to $R_5$ occupies position 4';
— pyridine derivatives wherein the NCS-group forms a substituent of the pyridine ring, and the radical —X—$R_1$ denotes an aralkylthio group;
— pyridine derivatives wherein the NCS-group forms a substituent of the pyridine ring, and the radical —X—$R_1$ denotes an aralkyloxy group;
— pyridine derivatives wherein the NCS-group forms a substituent of the pyridine ring, and the radical —X—$R_1$ denotes an aralkylamino group.

The following compounds have proved to have a particularly high anthelmintic activity:

2-methylmercapto-5-isothiocyanopyridine,
2-ethylmercapto-5-isothiocyanopyridine,
2-n-propylmercapto-5-isothiocyanopyridine, 2-isopropylmercapto-5-isothiocyanopyridine,
2n-butylmercapto-5-isothiocyanopyridine,
2-sec.butylmercapto-5-isothiocyanopyridine,
2-n-pentylmercapto-5-isothiocyanopyridine,
2-(1', 1'-dimethylpropylmercapto)-5-isothiocyanopyridine,
2-(3',3'-dimethylpropylmercapto)-5-isothiocyanopyridine,
2-n-hexylmercapto-5-isothiocyanopyridine,
2-cyclohexylmercapto-5-isothiocyanopyridine,
2-(1-ethyl-butylmercapto)-5-isothiocyanopyridine,
2-tert.hexylmercapto-5-isothiocyanopyridine,
2-n-heptylmercapto-5-isothiocyanopyridine,
2-tert.heptylmercapto-5-isothiocyanopyridine,
2-n-octylmercapto-5-isothiocyanopyridine,
2-n-decylmercapto-5-isothiocyanopyridine,
2-methoxy-5-isothiocyanopyridine,
2-ethoxy-5-isothiocyanopyridine,
2-iso-propoxy-5-isothiocyanopyridine,
2-n-butoxy-5-isothiocyanopyridine,
2-n-heptyloxy-5-isothiocyanopyridine,
2-(2'-(ethoxyethoxy)-5-isothiocyanopyridine,
2-n-pentylamino-5-isothiocyanopyridine,
2-N,N-diethylamino-5-isothiocyanopyridine,
2-n-hexylamino-5-isothiocyanopyridine,
3-iso-pentylamino-5-isothiocyanopyridine,
2-cyclohexylamino-5-isothiocyanopyridine,
2-N,N-di-n-propylamino-5-isothiocyanopyridine,
2-N,N-di-n-hexylamino-5-isothiocyanopyridine,
2-N,N-di-n-butylamino-5-isothiocyanopyridine,
2-phenylthio-5-isothiocyanopyridine,
2-(4'-methylphenylthio)-5-isothiocyanopyridine,
2-(3'-methylphenylthio)-5-isothiocyanopyridine,
2-(4'-tert.butylphenylthio)-5-isothiocyanopyridine,
2-(2'-isopropylphenylthio-3-isothiocyanopyridine,
2-(2',3'-dimethylphenylthio)-5-isothiocyanopyidine,
2-(2', 5'-dimethylphenylthio)-5-isothiocyanopyridine,
2-(4'-chlorophenylthio)-5-isothiocyanopyridine,
2-(4'-bromophenylthio)-5-isothiocyanopyridine,
2-benzylthio-5-isothiocyanopyridine,
2-benzylthio-3-isothiocyanopyridine,
2-)4'-methylbenzylthio)-5-isothiocyanopyridine,
2-(4'-methoxybenzyl(thio)-5-isothiocyanopyridine,
2-(4'-fluorobenzylthio)-5-isothiocyanopyridine,
2-(4'-chlorobenzylthio)-5-isothiocyanopyridine,
2-(2'-chlorobenzylthio)-5-isothiocyanopyridine,
2-(2',4'-dichlorobenzylthio)-5-isothiocyanopyridine,
2-(4'-bromobenzylthio)-5-isothiocyanopyridine,
2-(2'-phenylethylthio)-5-isothiocyanopyridine,
2-(3'-phenylpropylthio)-5-isothiocyanopyridine,
2-(6'-phenyl-hexylthio)-5-isothiocyanopyridine,
2-(4'-methylphenylsulphonyl)-5-isothiocyanopyridine,
2-(4'-tert.butylphenylsulphonyl)-5-isothiocyanopyridine,
2-(4'-chlorophenylsulphonyl)-5-isothiocyanopyridine,
2-(2',4'-dichlorobenzylsulphonyl)-5-isothiocyanopyridine, 2-phenoxy-5-isothiocyanopyridine,
2-(4'-methyl-phenoxy)-5-isothiocyanopyridine,
2-(3'-methyl-phenoxy)-5-isothiocyanopyridine,
2-(2'-methyl-phenoxy)-5-isothiocyanopyridine,
2-(4'-ethyl-phenoxy)-5-isothiocyanopyridine,
2-(4'-fluorophenoxy)-5-isothiocyanopyridine, 2-(3'-chlorophenoxy)-5-isothiocyanopyridine,
2-(2',4'-dichlorophenoxy-5-isothiocyanopyridine,
2-(3'-trifluoromethyl-phenoxy)-3-isothiocyanopyridine,
2-(4'-methoxy-phenoxy)-5-isothiocyanopyridine,
2-(4'-methoxy-phenoxy)-3-isothiocyanopyridine,
2-(3'-methoxy-phenoxy)-5-isothiocyanopyridine,
2-(4'-fluoroanilino)-5-isothiocyanopyridine,
2-(4'-chloroanilino)-5-isothiocyanopyridine,
2-(4'-bromoanilino)-5-isothiocyanopyridine,
2-(4'-methylanilino)-5-isothiocyanopyridine,
2-(4'-phenoxyanilino)-5-isothiocyanopyridine,
2-(4'-phenylanilino)-5-isothiocyanopyridine,
2-(4'-methoxyanilino)-5-isothiocyanopyridine,
2-(4'-ethoxyanilino)-5-isothiocyanopyridine.

The following are particularly highly effective as defoliating and desiccating agents:

2-n-butoxy-5-isothiocyanopyridine,
2-n-heptoxy-5-isothiocyanopyridine,
2-n-heptylthio-5-isothiocyanoparidine,
2-allylthio-5-isothiocyanopyridine,
2-butylthio-5-isothiocyanopyridine,
2-pentylthio-5-isothiocyanopyridine,
2-octylthio-5-isothiocyanopyridine,
2(2'-phenylethylthio)-5-isothiocyanopyridine.

The new active substances of formula I according to the invention have a wide range of action and are suitable for the control of parasitic nematodes of the orders:
　Dracunculoidea,
　Ascaroidea (e.g. *Ascaridia galli*),
　Trichinelloidea,
　Strongyloidea,
　Trichostrongyloidea,
　Metastrongyloidea,
as well as for the control of cestodes of the families:
　Dilepididae (e.g. *Hymenolepis nana*),
　Taeniidae,
　Diphyllobotridae,
and for the control of trematodes of the families:
　Dicrocoelidae,
　Fasciolidae (e.g. *Fasciola hepatica*)
　Schistosamatidae (e.g. *Schistosoma bovis*)
in the case of domestic and farm animals, such as cattle, sheep, goats, horses, pigs, cats, dogs and poultry. The new active substances can be administered in single doses to the animals, or in repeated doses, the single doses preferably being, depending on the species of the animal, between 25 and 1000 mg per kilogram of body weight. A better effect can be obtained in some cases by a protracted administration of the active substances, or smaller complete doses may suffice. The active substances or mixtures containing them can also be added to the feed or introduced into drinking troughs. The finished feed contains the substances of formula I preferably in a concentration of ca. 0.05 to 1.0 percent by weight.

The new active substances can be administered to the animals perorally or via the abomasum, e.g. in the form of solutions, emulsions, suspensions (drenches), powders, tablets, boluses and capsules. These preparations are prepared, for example, by use of the usual solid carriers, such as kaolin, talcum, bentonite, sodium chloride, calcium phosphate, carbohydrates, cellulose powder, cottonseed meal, carbowaxes and gelatine, or liquids such as water, optionally with the addition of surface-active substances such as ionic or nonionic dispersing agents, as well as oils, and other solvents and diluents harmless to the animal organism. If the anthelmintic agents are in the form of feed concentrates, then the carriers used are, for example, production feed, fodder grain or protein concentrates. Such feed concentrates or agents can contain, in addition to the active substances, also additives, vitamins, antibiotics, chemotherapeutical agents, or other pesticides, mainly bacteriostatics, fungistatics, coccidiostatics, also hormone preparations, substances having anabolic activity, or other substances promoting growth, affecting the quality of the meat of slaughter cattle, or being in some other way beneficial for the organism.

The following known anthelmintics, for example, can be used in combination with the described preparations:

Principally as nematocides:
Absonal
Alcopar
Anthelcide
Ascaridole
Badminth II
Bephenium
Bradosol
Cambendazol
Chlorophos
Chlorthion
Coumaphos
Cyanin
Destomycin
Diethylcarbamazine
Dichlorophene,
DDVP
1,4-di-(D-glucosyl)-piperazine
Dithiazonine
Dow ET/70
Dowco 132
Dymanthine . HCl
Egressin
Gainex
Hexachlorophene
Hexylresorcinol
Ionit
Levamisol
Mepacrine
Methylene violet
1-Methyl-1-tridecylpiperazinium-4-carboxylic acid ethyl ester
Methyridine
Monopar
Narlene
Neguvon
Nematodin
Nemural
Mebendazol
Nidanthel
Parbendazol
Parvex
Phenothiazine
Piperazine
Polymethylene-piperazine
Promethazine
Pyrantel
Pyrathiazine
Pyryinium-embonate Rametin
Ronnel
Santonin
Shell 1808
Stilbazium
Tetramisole
Thenium
Thiabendazole
Thymolan
Triclofenol
Treclofenol-piperazine
Vermella Principally as trematocides:

Acedist
Bilevon M
Bilevon R
Bithionol
Disophenol
Freon 112
Hetol
Hetolin
Hexachloroethane
Hexachlorophene
Hilomid
Niclofolan
Nitroxynil
Ranide
Tremerad
Tribromsalan (Tremasept II)
Zanil
Brotianid Principally as cestocides:

Acranil
Arecoline
Atebrin
Bithionol
Bithionol oxide
Bunamidine
Cestodin
Cambendazol
Dibutyltin dilaurate
Dichlorophen
Dioctyltin dichloride
Dioctyl tin laurate
Doda
Filixic acid
Hexachlorophene
Nidanthel
Terenol
Yomesan For combination with the active substances according to the invention, it is also possible to use preparations containing several active substances, e.g.:

| | |
|---|---|
| Eludon | Piperazine-hexahydrate + Copper sulphate + Sodium metaarsenite |
| Equizol A | Thiabendazole + Piperazine phosphate |
| Nilzan | Tetramisole + Zanil |
| Nitroarene | Yomesan + Dichlorophene |
| Parvec plus | Phenothiazine + Piperazine-CS$_2$-complex |
| Phenovis 2 | Phenylbenzimidazole + Phenothiazine |

Anthelmintic agents according to the invention, as well as agents for defoliation and desiccation, are produced in a manner known per se by the intimate mixing and grinding of active substances of the general formula I with suitable carriers, optionally with the addition of dispersing agents or solvents which are inert to the active substances. The active substances can be obtained and used in the following forms:

solid preparations: dusts, scattering agents, granulates, (coated granulates, impregnated granulates and homogeneous granulates);
water-dispersible concentrates of active substance: dispersible powders (wettable powders), pastes and emulsions;
liquid preparations: solutions.

The solid preparations (dusts, scattering agents or granulates) are produced by the mixing of the active substances with solid carriers. Suitable carriers are, for example, the above mentioned carriers, as well as bole, loess, chalk, limestone, ground limestone, dolomite, diatomaceous earth, precipitated silicic acid, alkaline-earth silicates, sodium and potassium aluminium silicates (feldspars and mica), calcium and magnesium sulphates, ground synthetic materials, ground vegetable products such as bran, bark dust, sawdust, ground nutshells, residues of plant extractions, active charcoal, etc., singly or as mixtures with each other.

For dusts the particle size of the carriers is advantageously up to ca. 0.1 mm; for scattering agents from ca. 0.075 mm to 0.2 mm; and for granulates 0.2 mm or coarser.

The concentration of active substance in the solid preparations is from 0.5 to 80%.

To these mixtures may also be added additives stabilising the active substance, and/or nonionic, anion-active and cation-active substances, which, for example, improve the adhesiveness of the active substances (adhesives and agglutinants), and/or ensure a better wettability (wetting agents) and dispersibility (dispersing agents). Suitable adhesives are, for example, the following: olein/lime mixture, cellulose derivatives (methyl cellulose), hydroxyethylene glycol ethers of monoalkyl and dialkyl phenols having 1 to 15 ethylene oxide radicals per molecule and 8 to 9 carbon atoms in the alkyl radical, ligninsulphonic acids, their alkali metal and alkaline-earth metal salts, polyethylene glycol ethers (carbowaxes), fatty alcohol polyethylene glycol ethers having 5 to 20 ethylene oxide radicals per molecule and 8 to 18 carbon atoms in the fatty alcohol moiety, condensation products of ethylene oxide, propylene oxide, polyvinyl pyrrolidones, polyvinyl alcohols, condensation products of urea and formaldehyde, as well as latex products.

Water-dispersible concentrates of active substance, i.e. wettable powders, pastes and emulsion concentrates, are agents which can be diluted with water to obtain any desired concentration. They consist of active substance, carrier, optionally additives which stabilize the active substance, surface-active substances, and anti-foaming agents and, optionally, solvents. The concentration of active substance in these agents is 5 to 80%.

The wettable powders and pastes are obtained by the mixing and grinding of the active substances with dispersing agents and pulverulent carriers, in suitable devices, until homogeneity is attained. Suitable carriers are, e.g. those previously mentioned in the case of solid preparations. It is advantageous in some cases to use mixtures of different carriers. Dispersing agents can be, e.g.: condensation products of sulphonated naphthalene and sulphonated naphthalene derivatives with formaldehyde, condensation products of naphthalene or of naphthalenesulphonic acids with phenol and formaldehyde, as well as alkali, ammonium and alkaline-earth metal salts of ligninsulphonic acid, also alkylarylsulphonates, alkali metal salts and alkaline-earth metal salts of dibutyl naphthalenesulphonic acid, fatty alcohol sulphates, such as salts of sulphated hexadecanols, heptadecanols, octadecanols, and salts of sulphated fatty alcohol glycol ether, and sodium salt of oleyl cthionate, the sodium salt of oleyl methyl tauride, ditertiary acetylene glycols, dialkyl dilauryl ammonium chloride, and fatty acid alkali-metal and alkaline-earth metal salts.

Suitable anti-foaming agents are, for example, silicones.

The active substances are so mixed, ground, sieved and strained with the above mentioned additives that the solid constituent in the case of wettable powders has a particle size not exceeding 0.02 to 0.04 mm, and in the case of pastes not exceeding 0.03 mm. Dispersing agents such as those mentioned in the preceding paragraphs, organic solvents and water are used in the preparation of emulsion concentrates and pastes. The solvents must be practically odourless, non-phytotoxic and inert to the active substances.

Furthermore, the agents according to the invention can be administered to the animals, orally or parenterally, in the form of solutions. For this purpose, the active substance (or several active substances) of the general formula I is (or are) dissolved or emulsified in suitable organic solvents, solvent mixtures or water. Suitable organic solvents are solvents which are non-toxic and inert to the active substances. The solutions are to contain the active substance in a concentration of from 1 to 20%.

Isothiocyanopyridines of formula I can be produced according to the invention by a process in which the basic aminopyridines of formula II

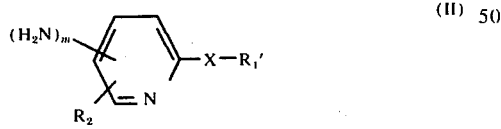
(II)

wherein
R$_1$' represents hydrogen, a straight-chain or branched alkyl or alkenyl radical having 1 to 17 carbon atoms, which can be substituted by halogen, hydroxyl, lower alkoxy, phenoxy, lower alkylthio, lower alkylamino, di-lower alkylamino, cycloalkyl having 3 to 6 carbon atoms, alkanoyl having 1 to 6 carbon atoms, or by a benzoyl radical optionally substituted by lower alkyl, halogen, trifluoromethyl or nitro, a mono-, bi- or tricyclic cycloalkyl or cycloalkenyl radical having 3 to 10 carbon atoms in the ring structure, optionally mono- or disubstituted by lower alkyl, whereby bi- and tricyclic radicals can be bound also by way of a methylene group to the group X, or a radical of the formula

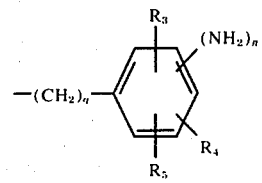

wherein R$_3$, R$_4$, R$_5$ and $q$ have the meanings given above, and in each case one of the symbols m and n denotes 1 while the other is 0, are a. reacted with a thiocarbonic acid derivative of the formula

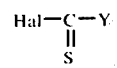

wherein Hal represents chlorine or bromine, and Y chlorine, bromine or a dialkylamino group; or b. reacted with a sulphide of the formula

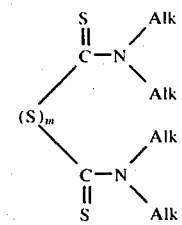

wherein Alk denotes a lower alkyl radical having at most 4 carbon atoms; or c. reacted with pentathio-dipercarbonic acid-bis-(trihaloalkyl)-esters; or d. reacted with phosgene and phosphorus pentasulphide in a solvent or diluent inert to the reactants; or e. converted with benzoylisothiocyanate into the corresponding thiourea, and this thermally decomposed in the presence of a solvent inert to the reactants, preferably in an aromatic hydrocarbon or halogenated hydrocarbon, or in the presence of acids or acid anhydrides; or f. converted with carbon disulphide in the presence of an inorganic base, or of an amine, into the corresponding dithiocarbamic acid salts, and these then dehydrosulphated; or g. reacted with carbon disulphide in the presence of carbodiimides and of a tertiary amine; or h. reacted with ammonium rhodanide in the presence of gaseous hydrogen chloride.

The processes are performed in solvents or diluents which are inert to the reactants.

The following, for example, can be used in the process according to the invention:
aliphatic and aromatic hydrocarbons, aliphatic and aromatic halogenated hydrocarbons, ethers and ethereal compounds such as dioxane or tetrahydrofuran, ketones, amides such as dimethylformamide, etc., water, or mixtures of such solvents with water.

In the preparation of isothiocyano compounds of formula I by the methods given under a) - h), temperatures of between −20° and +100° C are maintained, preferably of between −10° and +30° C, and with application of a dialkylthiocarbamoyl halide such as diethylthiocarbamoyl chloride, or in the case of thermal decomposition according to method e), higher temperatures of between 40° and 200° C are used.

The formation of the isothiocyano group involves known methods: reactions of amines with thiophosgene (a) are described in Houben-Weyl, 4th edition, Vol. 9, p. 876 (1955), the use of acid-binding agents by O. E. Schultz in Arch. Pharm. 295, 146-151 (1962); the reaction of amines with N,N-diethylthiocarbamoyl chloride (a) has been described in Jouranl org. Chem. 30, 2465 (1965), that with bis-thiocarbamoyl sulphides (b) by F. H. Marquardt in Helv. chim. Acta 49, 1716 (1966), and that with pentathiodipercarbonic acid-bis-(trihalogenoalkyl)-ester (c) by R. Gottfried in Agnew. Chem. 78, 985 (1966), and that with phosgene and phosphorus pentasulphide according to Houben-Weyl, 4th edition, Vol. 9, p. 867 ff.

The preferred solvents for the reactions given under d) and e) are o-dichlorobenzene and chlorobenzene; other dichlorobenzenes, toluene, xylenes, cumol, etc. are however also suitable. The thermal decomposition of thioureas e) is performed in the manner described by J. N. Baxter et al. in J. Chem. Soc. (1956), p. 659 ff.. The thioureas are produced to Org. Syntheses III, 735, (1955). The inorganic bases used in the production of dithiocarbamic acid salts (f) are, e.g. the hydroxides, oxides and carbonates of alkali and alkaline-earth metals, as well as ammonium hydroxide; and the amines used are, e.g. trialkylamines, pyridine bases or ammonia (cp. C.A. 70, 3389 q (1969), etc.. Dehydrosulphuration (c) can be carried out oxidatively with metal salts (Brit. Patent No. 793,802, Dutch Patent No. 81,326), e.g. with lead, copper, zinc or iron-III salts, iodine, alkali metal hypochlorites and -chlorites, preferably with those of potassium and sodium (French Patent No. 1,311,855), also with suitable acid halides such as phosgene and phosphorus oxychloride (D. Martin et. al. Chem. Ber 98, 2425-2426 (1965)), as well as with elementary chlorine and ammonium sulphide (DAS 1,192,139) or chloramine T (British Patent No. 1,024,913).

Isothiocyanopyridines of formula I are obtainable, for example, by reaction of aminopyridines with thiophosgene in suitable organic solvents, water and mineral acids, preferably in dilute hydrochloric acid, according to:

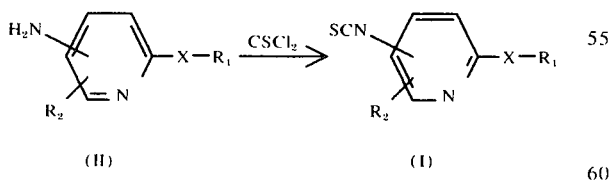

The reaction with thiophosgene can also be smoothly performed in the presence of an acid-binding agent, such as an organic base, e.g. triethylamine, pyridine, N,N-dimethylaniline, or an inorganic weak base, such as $CaCO_3$, $BaCO_3$, Na-acetate, $NaHCO_3$ or $KH_2PO_4$. A subsequent treatment with one of the mentioned acid-binding agents is also possible in the case where, in the reaction with thiophosgene in organic solvents, water or dilute mineral acid, the effective salts are firstly obtained.

Salts of isothiocyanopyridines of formula I can be prepared with strong acids. Salts with weak or diluted acids are producible if one or both substituents $R_1$ and $R_2$ carries or carry a basic group, or if X is

The hydrochlorides of this last-mentioned sub-group can also be obtained direct, starting with amino compounds of formula II, if thiophosgene is used for the reaction in organic solvents, wateer or dilute hydrochloric acid.

Aminopyridines of formula II and their immediate precursors, the nitropyridines, are in some cases known or can be produced by known methods. [cp. Gifu Yakka Daigaku 13, 34–37 (1963)]; Rocz. Chem. 42, 795–801 (1968); Yakugaku Zasshi 78, 1447–1448 (1958), J. Chem. Soc. 1948 (1939–1945); J. Pharm. Soc. Japan 62, 140–143 (1942); J. Pharm. Soc. Japan 64, N. 7A, 10–11 (1944); J. Pharm. Soc. Japan 72, 1017–1020, (1952); Brit. Pat. 870027 Chem. Listy, 49, 731–736; Collection Czechoslov. Chem. Communs. 20, 1221–6 (1955); J. Pharm. Soc. Japan 71, 786–789 (1951); J. Pharm. Soc. Japan 72, 1141–1144 (1952); J. Sci. Ind. R s. (India) 21 B, 483–486 (1962); Seifen-Oele-Fette-Wachse 91 (12), 593–595 (1965); Ricerca sci. 8 I, 427–429 (1937); Gazz. chim. ital. 69, 86–96 (1939).

EXAMPLE 1

Preparation of
2-methylmercapto-5-isothiocyano-pyridine (Compound 1)

26.2 g of crude 2-methylmercapto-5-amino-pyridine, obtained by catalytic hydrogenation, is dissolved in 200 ml of dioxane. This solution is added dropwise in the course of 20 minutes at room temperature to a mixture of 23.4 g of thiophosgene and 200 ml of dioxane, whereby a slightly exothermic reaction is observed. The solution is further stirred overnight, and then stirred into 1.5 liters of ice water. The crystalline precipitate is chromatographed through silica gel, and extracted with methylene chloride. The pure final product melts at 63°–65° C.

EXAMPLE 2

Preparation of
2-ehtylsulphonyl-5-isothiocyano-pyridine (Compound 25)

30.8 g of crude 2-ethylsulphonyl-5-amino-pyridine, obtained by catalytic hydrogenation, is dissolved in 250 ml of dioxane. This solution is added dropwise during 15 minutes at room temperature to a mixture of 23 g of thiophosgene and 300 ml of dioxane. The solution is stirred overnight and then stirred into 1.5 liters of ice water. The crystalline precipitate is chromatographed with methylene chloride through silica gel to obtain the pure final product, M.P. 108°–111° C.

EXAMPLE 3

Preparation of 2-methoxy-5-isothiocyano-pyridine (Compound No. 32)

24.8 g of crude 2-methoxy-5-amino-pyridine, obtained by catalytical hydrogenation, is dissolved in 200 ml of dioxane. This solution is added at room temperature to a mixture of 25 g of thiophosgene and 200 ml of dioxane, whereby a slight exothermic reaction is observed. The solution is further stirred overnight, and then stirred into 1.5 liters of ice water. Neutralisation is performed in the cold state with 2N NaOH, and the crystalline precipitate chromatographed with methylene chloride through silica gel. The pure final product melts at 58°–60° C and has the following structure:

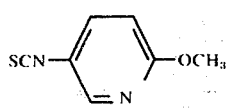

EXAMPLE 4

Preparation of 2-n-hexylamino-5-isothiocyanopyridine (Compound No. 58)

a. 101 g of triethylamine and subsequently 50 g of n-hexylamino are placed into 600 ml of distilled anhydrous ethanol. An amount of 79 g of 2-chloro-5-nitropyridine is added portionwise at room temperature in the course of 15 minutes. The mixture is then heated to reflux temperature, whereby it goes into solution at 60° C. The solution is stirred for 24 hours at the reflux temperature and afterwards cooled to room temperature; the solution is poured into ice/water, and the formed precipitate filtered off. The 2-n-hex-ylamino-5-nitropyridine obtained after recrystallisation from ethanol/water melts at 56°–57° C.

b. 99 g of 2-n-hexylamino-5-nitropyridine is dissolved in 1000 ml of distilled ethanol and, after addition of 10 g of Raney nickel, hydrogenated at room temperature to 40° C. With 13% and 85% hydrogen absorption, there are additionally added 10 g and 5 g, respectively, of 5% Pt-C. Raney nickel and platinum are filtered off under suction and ethanol completely removed from the filtrate. The formed 2-n-hexylamino-5-aminopyridine is sufficiently pure for the next step.

c. 60 g of 2-n-hexylamino-5-aminopyridine in 300 ml of distilled anhydrous dioxane is added dropwise, within 20 minutes at 13°–15° C. to a solution of 42.77 g of thiophosgene in 400 ml of dioxane. The mixture is stirred at room temperature for 10 hours. It is then poured into ice/water, and the pH-value adjusted with solid sodium bicarbonate to pH 8 – 9. The precipitate is filtered off and washed neutral with water. Recrystallised from pyridine/water, the resulting 2-n-hexylamine-5-isothiocyanopyridine melts at 53°–55° C.

The following isothiocyanopyridines of formula Ia can be prepared in the same manner as that described in Example 1:

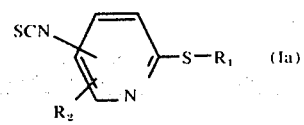

| Comp. No. | SCN-position | $R_2$ | $R_1$ | Physical characteristics |
|---|---|---|---|---|
| 1 | 5 | H | $CH_3$ | mp. 63-65° C |
| 2 | 5 | H | $CH_2CH_3$ | $n_D^{20}$ 1,670 |
| 3 | 3 | 6-Cl | $CH_2CH_3$ | |
| 4 | 5 | H | n-$C_3H_7$ | $n_D^{20}$ 1,666 |
| 5 | 5 | H | iso-$C_3H_7$ | $n_D^{20}$ 1,6694 |
| 6 | 5 | H | n-$C_4H_9$ | $n_D^{20}$ 1,6548 |
| 7 | 5 | H | sec.$C_4H_9$ | $n_D^{20}$ 1,670 |
| 8 | 5 | H | $C(CH_3)_3$ | mp. 70-72° C |
| 9 | 5 | H | n-$C_5H_{11}$ | $n_D^{20}$ 1,6212 |
| 10 | 5 | H | $C(CH_3)_2CH_2-CH_3$ | $n_D^{20}$ 1,6418 |
| 11 | 5 | H | $CH_2CH_2CH(CH_3)_2$ | $n_D^{20}$ 1,6371 |
| 12 | 5 | H | n-$C_6H_{13}$ | $n_D^{20}$ 1,6215 |
| 13 | 5 | H | –⟨H⟩ | mp. 58-60° C |
| 14 | 5 | H | $CH(CH_2CH_3)CH_2CH_2CH_3$ | $n_D^{20}$ 1,6255 |
| 15 | 5 | H | $CH_2CH_2C(CH_3)_3$ | $n_D^{20}$ 1,6168 |
| 16 | 5 | H | n-$C_7H_{15}$ | $n_D^{20}$ 1,6089 |
| 17 | 5 | H | $CH_2CH_2CH_2C(CH_3)_3$ | $n_D^{20}$ 1,6279 |
| 18 | 5 | H | n-$C_8H_{17}$ | $n_D^{20}$ 1,6000 |
| 19 | 5 | H | n-$C_{10}H_{21}$ | $n_D^{20}$ 1,5883 |
| 20 | 5 | H | n-$C_{12}H_{25}$ | mp. 42-44° C |
| 21 | 5 | H | n-$C_{14}H_{29}$ | |
| 22 | 5 | H | n-$C_{15}H_{31}$ | |
| 23 | 5 | H | $CH_2CH_2N(C_2H_5)_2$ | |
| 24 | 5 | H | $CH_2-CH_2-CH_2-OC_6H_5$ | |

The following isothiocyanopyridines of formula Ib can be prepared in the same manner as that described in Example 2:

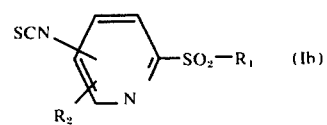

| Comp. No. | SCN-position | $R_2$ | $R_1$ | Physical characteristics |
|---|---|---|---|---|
| 25 | 5 | H | $CH_3$ | |
| 26 | 5 | H | $C_2H_5$ | mp. 108-111° C |
| 27 | 5 | H | $C(CH_3)_3$ | |

The following isothiocyanopyridines of formula Ic can be prepared in the same manner as that described in formula 3:

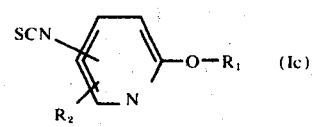

| Comp. No. | SCN-position | $R_2$ | $R_1$ | Physical characteristics |
|---|---|---|---|---|
| 32 | 5 | H | $CH_3$ | mp. 58–60° C |
| 33 | 3 | H | $CH_3$ | mp. 38–39° C |
| 34 | 5 | 6-$CH_3O$ | $CH_3$ | |
| 35 | 5 | H | $C_2H_5$ | mp. 59–61° C |
| 36 | 3 | H | $C_2H_5$ | mp. 30–31° C |
| 37 | 5 | 6-$C_2H_5O$ | $C_2H_5$ | |
| 38 | 5 | H | n-$C_3H_7$ | $n_D^{20}$ 1,608 |
| 39 | 5 | H | iso-$C_3H_7$ | $n_D^{20}$ 1,605 |
| 40 | 5 | H | n-$C_4H_9$ | $n_D^{20}$ 1,666 |
| 41 | 5 | H | n-$C_6H_{13}$ | |
| 42 | 5 | H | n-$C_7H_{15}$ | |
| 43 | 5 | H | n-$C_{10}H_{21}$ | |
| 44 | 5 | H | n-$C_{12}H_{25}$ | |
| 45 | 5 | H | $-CH_2CH_2-OCH_3$ | |
| 46 | 5 | 6-Cl | $-CH_2CH_2-OCH_3$ | mp. 51–53° C |
| 47 | 5 | H | $-CH_2CH_2-OCH_2CH_3$ | mp. 52–53° C |

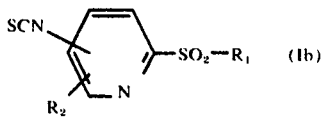

| Comp. No. | SCN-position | $R_2$ | $R_1$ | Physical characteristics |
|---|---|---|---|---|
| 28 | 5 | H | n-$C_7H_{15}$ | |
| 29 | 5 | H | n-$C_{10}H_{21}$ | |
| 30 | 5 | H | n-$C_{12}H_{25}$ | mp. 88–90° C |
| 31 | 5 | H | n-$C_{14}H_{29}$ | |

In the same manner as that described in Example 4 are prepared the following isothiocyanopyridines of formula Id, from which corresponding acid addition salts are obtainable:

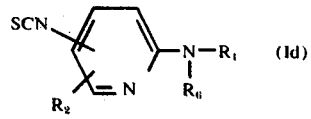

| Comp. No. | SCN-position | $R_2$ | $NR_6$ | $R_1$ | Physical characteristics |
|---|---|---|---|---|---|
| 48 | 5 | H | —N—H | H | |
| 49 | 5 | H | —N—H | $CH_3$ | 103–105° C |
| 50 | 5 | H | —N—H | $C_2H_5$ | 100–101° C |
| 51 | 5 | H | —N—H | n-$C_3H_7$ | 85–90° C |
| 52 | 5 | H | —N—H | iso-$C_3H_7$ | 78–81° C |
| 53 | 5 | H | —N—H | n-$C_4H_9$ | 43–46° C |
| 54 | 5 | H | —N—H | iso-$C_4H_9$ | 59–63° C |
| 55 | 5 | H | —N—H | sec-$C_4H_9$ | $n_D^{20}$ 1,6428 |
| 56 | 5 | H | —N—H | n-$C_5H_{11}$ | 54–56° C |
| 57 | 5 | H | —N—H | iso-$C_5H_{11}$ | 58–63° C |
| 58 | 5 | H | —N—H | n-$C_6H_{13}$ | 53–55° C |
| 59 | 5 | H | —N—H | n-$C_7H_{15}$ | |
| 60 | 5 | H | —N—H | n-$C_8H_{17}$ | 68–71° C |
| 61 | 5 | H | —N—H | n-$C_9H_{19}$ | |
| 62 | 5 | H | —N—H | n-$C_{10}H_{21}$ | 70–75° C |
| 63 | 5 | H | —N—H | n-$C_{11}H_{23}$ | 67–69° C |
| 64 | 5 | H | —N—H | n-$C_{12}H_{25}$ | 73–75° C |
| 65 | 5 | H | —N—H | n-$C_{13}H_{27}$ | |
| 66 | 5 | H | —N—H | n-$C_{14}H_{29}$ | 62–65° C |
| 67 | 5 | H | —N—H | n-$C_{15}H_{31}$ | |
| 68 | 5 | H | —N—$CH_3$ | $CH_3$ | 57–61° C |
| 69 | 5 | H | —N—$C_2H_5$ | $C_2H_5$ | 49–53° C |
| 70 | 5 | H | —N(n-$C_3H_7$) | n-$C_3H_7$ | $n_D^{20}$ 1,6328 |
| 71 | 5 | H | —N(n-$C_4H_9$) | n-$C_4H_9$ | $n_D^{20}$ 1,6125 |
| 72 | 5 | H | —N(n-$C_5H_{11}$) | n-$C_5H_{11}$ | |
| 73 | 5 | H | —N(n-$C_6H_{13}$) | n-$C_6H_{13}$ | $n_D^{20}$ 1,5790 |
| 74 | 5 | H | —N(n-$C_8H_{17}$) | n-$C_8H_{17}$ | $n_D^{20}$ 1,5625 |
| 75 | 5 | H | —N(n-$C_{10}H_{21}$) | n-$C_{10}H_{21}$ | $n_D^{20}$ 1,5476 |
| 76 | 5 | H | —N(n-$C_{13}H_{23}$) | n-$C_{11}H_{23}$ | $n_D^{20}$ 1,5434 |
| 77 | 5 | H | —N(n-$C_{12}H_{27}$) | n-$C_{13}H_{27}$ | $n_D^{20}$ 1,5358 |
| 78 | 5 | H | —N($CH_3$) | n-$C_8H_{17}$ | $n_D^{20}$ 1,6427 |
| 79 | 5 | H | —NH | Cyclopentyl | mp. 65–67° C |
| 80 | 5 | H | —NH | Cyclohexyl | mp. 98–101° C |
| 81 | 5 | H | | —N⟨⟩O (morpholino) | mp. 116–118° C |

-continued

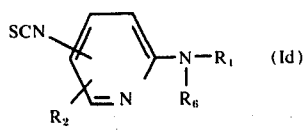

| Comp. No. | SCN-position | R₂ | NR₆ | R₁ | Physical characteristics |
|---|---|---|---|---|---|
| 82 | 5 | H | | —N(piperidinyl) | |
| 83 | 5 | H | | —N(4-methylpiperidinyl) | |
| 84 | 5 | H | | —N(2,6-dimethylpiperidinyl) | |
| 85 | 5 | H | | —N(4-propylpiperidinyl) | |
| 86 | 5 | H | —NH | Cyclopropyl | |
| 87 | 5 | H | —NH | Allyl | |
| 88 | 5 | H | —NCH₃ | $CH_2$—$CH_2$—CN | |
| 89 | 5 | H | | —N(2-methylaziridinyl) | |
| 90 | 5 | H | —NH | $CH_2CH_2$—$OCH_3$ | |
| 91 | 5 | H | —NH | $CH_2(CH_2)_2$—O—$CH_3$ | |
| 92 | 5 | H | —NH | $CH_2$—$CH_2$—NH—$C_2H_5$ | |
| 93 | 5 | H | —NH | $CH_2$—$CH_2N(CH_3)_2$ | |
| 94 | 5 | H | —NH | $CH_2$—$(CH_2)_2$—$NHCH_3$ | |
| 95 | 5 | H | —NH | $CH_2$—$(CH_2)_2$—$OC_2H_5$ | |
| 96 | 5 | H | —NH | $CH_2(CH_2)_3$—$NHC_2H_5$ | |
| 97 | 5 | H | —NH | $CH_2(CH_2)_2$—$N(CH_3)_2$ | |
| 98 | 5 | H | —NH | $CH_2(CH_2)_2O(CH_2)_2$—$CH_3$ | |
| 99 | 5 | H | —NH | $CH_2$—$(CH_2)_2NH(CH_2)_3CH_3$ | |
| 100 | 5 | H | —NH | $CH_2$—$(CH_2)_2N(C_2H_5)_2$ | |
| 101 | 5 | H | —NH | $CH_2CH(C_2H_5)(CH_2)_3CH_3$ | |
| 102 | 5 | H | —NH | $(CH_2)_4$—cyclohexyl | |
| 103 | 5 | H | —NH | 4-tert-butylcyclohexyl | |
| 104 | 3 | H | —NH | —$CH_3$ | |
| 105 | 3 | H | —NH | $C_6H_{13}$ | |
| 106 | 3 | H | —NH | $C_{14}H_{29}$ | |
| 107 | 3 | H | —$CH_3$ | $CH_3$ | |
| 108 | 3 | H | —N(n-$C_6H_{13}$) | n-$C_6H_{13}$ | |
| 109 | 5 | H | | —N(4-benzylpiperidinyl) | |
| 110 | 5 | H | | —N(pyrrolyl) | |
| 111 | 5 | H | | —N(imidazolinyl) | |
| 112 | 3 | H | morpholino | | |
| 113 | 3 | H | N($C_2H_5$) | $C_2H_5$ | |

EXAMPLE 5

Preparation of
2(4'-tert.butylphenylthio)-5-isothiocyanopyridine (Compound No. 1.9)

25.8 g of crude 2-(4'-tert.butylphenylthio)-5-aminopyridine, obtained by catalytic hydrogenation, is dissolved in 200 ml of dioxane. This solution is added dropwise at room temperature, in the course of 10 minutes, to a mixture of 12.5 g of thiophosgene in 200 ml of dioxane, the temperature rising to 30° C. The solution is stirred overnight and subsequently stirred into 1 liter of ice water. The solution is neutralised with 2N NaOH. The crystalline precipitate is purified by means of column-chromatography through silica gel, with methylene chloride as the eluant. The pure product melts at 92°– 93.5° C and has the following structure:

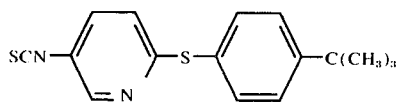

EXAMPLE 6

Preparation of 2-benzylthio-5-isothiocyano-pyridine (Compound No. 1.19)

a. 91.4 g of 2-benzylthio-5-nitropyridine is dissolved in 1 liter of dimethylformamide and, after addition of 20 g of Raney nickel, hydrogenated at room temperature and at 20°–30° until the reaction is completed. The Raney nickel is filtered off under nitrogen by suction; the solvent is then evaporated off under vacuo to obtain 2-benzylthio-5-amino-pyridine, which is used direct for the subsequent thiophosgenisation.

b. 76.7 g of 2-benzylthio-5-amino-pyridine in 200 ml of dioxane is added dropwise at 24°–35° C, in the course of 20 minutes, to a solution of 46.2 g of thiophosgene in 300 ml of dioxane; stirring is subsequently continued for 12 hours at room temperature. The solution is then stirred into 1 liter of ice water, and the formed precipitate filtered off under suction. After purification by chromatography with methylene chloride through silica gel, the final product melts at 58°–60°C.

EXAMPLE 7

Preparation of
2-(4'-chlorophenylsulphonyl)-5-isothiocyano-pyridine (Compound No. 2.3)

a. 53.5 g of 2-(4'-chlorophenylthio-5-nitro-pyridine is added portionwise at room temperature to a solution of 500 ml of glacial acetic acid, 48 ml of H₂O₂(33%) and 4 ml of conc. H₂SO₄. After 24 hours, the solution is stirred into 2 litres of ice water: the resulting precipitate is filtered off under suction, and chromatographed through silica gel. The product then has a melting point of 187°–189° C and is pure.

24.5 g of 2-(4'-chlorophenylsulphonyl)-5-nitro-pyridine is dissolved in 300 ml of ethanol, and the solution, after the addition of 3 g of Raney nickel, hydrogenated at a temperature of between 20°and 35° C until the reaction ceases. Raney nickel is filtered of under nitrogen by suction. The solvent is evaporated off under vacuo to obtain 2-(4'-chlorophenylsulphonyl)-5-amino-pyridine, which is further processed in the crude state.

c. A solution of 14 g of 2-(4'-chlorophenylsulphonyl)-5-amino-pyridine is added dropwise at room temperature, in the course of 10 minutes, to a solution of 6.6 g of thiophosgene in 100 ml of dioxane, and stirring is then continued for 12 hours at the same temperature. The solution is then stirred into 500 ml of ice water; filtration under suction is performed and purification by chromatography with methylene chloride through silica gel; M.P. of product 163°–165° C.

EXAMPLE 8

Preparation of 2-phenoxy-5-isothio-cyanopyridine (Comp. 3.1)

18.6 g of crude 2-phenoxy-5-amino-pyridine, obtained by catalytic hydrogenation, is dissolved in 200 ml of dioxane. This solution is added dropwise at room temperature, in the course of 15 minutes, to a mixture of 12.5 g of thiophosgene in 200 ml of dioxane. The solution is further stirred overnight, and then stirred into 1 liter of ice water; the solution is neutralised with 2N NaOH, and the crystalline precipitate chromatographed through silica gel, with methylene chloride as the eluant. The resulting pure final product melts at 42°–43° C.

EXAMPLE 9

Preparation
2-(4'-methoxyanilino)-5-isothiocyano-pyridine (Compound No. 4.40)

a. 24.62 g of p-anisidine is placed into 300 ml of distilled anhydrous ethanol, and 20.2 g of triethylamine then slowly added dropwise. The mixture is heated to 60° C and, at this temperature, 31.7 g of 2-chloro-5-nitropyridine stirred in portionwise. Stirring in subsequently maintained during 90 minutes at reflux temperature. The solution is cooled to room temperature and poured into ice water; the precipitate is then filtered off and washed well with water. After recrystallisation from ethanol/water, the resulting 2-(4'-methoxyanilino)-5-nitropyridine melts at 155°–157° C.

b. 62.4 g of 2-(4'-methoxyanilino)-5-nitropyridine is dissolved in 550 ml of distilled ethanol and, after the addition of 5 g of Raney nickel, the solution hydrogenated at room temperature to 35° C. With 33% hydrogen absorption, a further 6 g of Raney nickel is added. The Raney nickel catalyst is filtered off with suction, and the ethanol completely removed from the filtrate. The resultant 2-(4'-methoxyanilino)-5-aminopyridine is sufficiently pure for the next step.

c. 50 g of 2-(4'-methoxyanilino)5-aminopyridine in 300 ml of distilled anhydrous dioxane is added dropwise at 15° C, within 15 minutes, to a solution of 26.8 g of thiophosgene in 200 ml of dioxane. The mixture is subsequently stirred at room temperature for 15 hours; it is then poured into ice/water, and the mixture adjusted to pH 8 with solid sodium bicarbonate. The precipitate is filtered off and washed neutral with water. The solid substance is dissolved in methylene chloride, and the organic phase washed with water and dried with magnesium sulphate. The solution is concentrated in a rotary evaporator, and the resulting product purified by column-chromatography through silica gel, with methylene chloride as the eluant.

The 2-(4'-methoxyanilino)-5-isothiocyanopyridine thus obtained melts at 137°–139° C.

The following isothiocyanopyridines of formula Ia can be prepared in the same manner as that described in Examples 5 and 6:

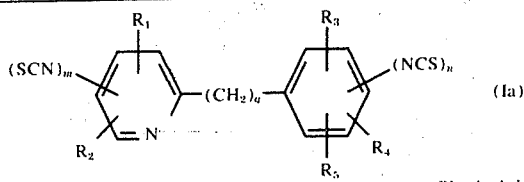

(Ia)

| Comp. No. | Compound | Physical data |
|---|---|---|
| 1.1 | 2-Phenylthio-5-isothiocyano-pyridine | M.P. 52–54° C |
| 1.2 | 6-Phenylthio-3-isothiocyano-pyridine | M.P. 82–84° C |
| 1.3 | 4-(4'-Isothiocyanophenylthio)-pyridine | M.P. 70–72° C |
| 1.4 | 2-(4'-Methylphenylthio)-5-isothiocyano-pyridine | M.P. 63–67° C |
| 1.5 | 2-(3'-Methylphenylthio)-5-isothiocyano-pyridine | M.P. $n_D^{25}$ 1.668 |
| 1.6 | 2-(4'-Methylphenylthio)-3-isothiocyano-pyridine | M.P. 66–67° C |
| 1.7 | 2-(2'-Isopropylphenylthio)-5-isothiocyano-pyridine | M.P. 38–40° C |
| 1.8 | 2-(2'-Isopropylphenylthio)-3-isothiocyano-pyridine | M.P. 60–62° C |
| 1.9 | 2-(4'-tert.Butylphenylthio)-5-isothiocyano-pyridine | M.P. 92–93.5° C |
| 1.10 | 2-(4'-Fluorophenylthio)-5-isothiocyano-pyridine | |
| 1.11 | 2-(4'-Chlorophenylthio)-5-isothiocyano-pyridine | M.P. 60–61.5° C |
| 1.12 | 2-(4'-Chlorophenylthio)-3-isothiocyano-pyridine | M.P. 59–60° C |
| 1.13 | 4-(2'-Chloro-4'-isothiocyanophenylthio-pyridine | M.P. 85–87° C |
| 1.14 | 2-(4'-Bromophenylthio)-5-isothiocyano-pyridine | M.P. 65–67° C |
| 1.15 | 2-(4'-Isothiocyanophenyl)-5-nitro-pyridine | M.P. 140–141° C |
| 1.16 | 2-(2',5'-Dimethylphenylthio)-5-isothiocyano-pyridine | |
| 1.17 | 2-(2,3-Dimethylphenylthio)-5-isothiocyano-pyridine | M.P. 41–42° C |
| 1.18 | 2-(2,5-Dichlorophenylthio)-5-isothiocyano-pyridine | M.P. 71–73° C |
| 1.19 | 2-Benzylthio-5-isothiocyano-pyridine | M.P. 58–60° C |
| 1.20 | 2-Benzylthio-3-isothiocyano-pyridine | M.P. 36–37° C |
| 1.21 | 3-Isothiocyano-4-benzylthio-pyridine | |
| 1.22 | 2-(4'-Methylbenzylthio)-5-isothiocyano-pyridine | M.P. 54–56° C |
| 1.23 | 2-(4'-Isothiocyanobenzylthio)-4-methyl-pyridine | |
| 1.24 | 2-(4'-Methoxybenzylthio)-5-isothiocyano-pyridine | M.P. 58–60° C |
| 1.25 | 2-(4'-Fluorobenzylthio)-isothiocyano-pyridine | M.P. 62–64° C |
| 1.26 | 2-(2'-Fluorobenzylthio)-5-isothiocyano-pyridine | |
| 1.27 | 2-(4'-Fluorobenzylthio)-3-isothiocyano-pyridine | |
| 1.28 | 2-(4'-Fluorobenzylthio)-3-isothiocyano-6-chloropyridine | |
| 1.29 | 2-(4'-Fluorobenzylthio)-3-isothiocyano-6-methoxy-pyridine | |
| 1.30 | 2-(4'-Fluorobenzylthio)-5-isothiocyano-6-methoxy-pyridine | |
| 1.31 | 2,6-Di-(4'-Fluorobenzylthio)-5-isothiocyano-pyridine | |
| 1.32 | 2-(4'-Chlorobenzylthio)-5-isothiocyano-pyridine | M.P. 60–62° C |
| 1.33 | 2-(4'-Chlorobenzylthio)-5-isothiocyano-6-methoxy-pyridine | |
| 1.34 | 2-(4'-Chlorobenzylthio)-3-isothiocyano-6-methoxy-pyridine | |
| 1.35 | 2-(4'-Chlorobenzylthio)-5-isothiocyano-6-diethylamino-pyridine | |
| 1.36 | 2-(4'-Methoxycarbonylaminophenylthio)-isothiocyano-pyridine | M.P. 119–121° C |
| 1.37 | 2-(2'-Chlorobenzylthio)-5-isothiocyano-pyridine | M.P. 74–76° C |
| 1.38 | 2-(4'-Bromobenzylthio)-5-isothiocyano-pyridine | M.P. 70–72° C |
| 1.39 | 2-(4'-Benzylthiobenzylthio)-5-isothiocyano-pyridine | |

-continued

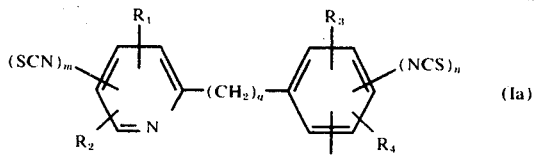

(Ia)

| Comp. No. | Compound | Physical data |
|---|---|---|
| 1.40 | 2-(2',4'-Dichlorobenzylthio)-5-isothiocyano-pyridine | M.P. 103–105° C |
| 1.41 | 2-(2'-Phenylethylthio)-5-isothiocyano-pyridine | $n_D^{25}$ 1,666 |
| 1.42 | 2-(1'-Phenylethylthio)-5-isothiocyano-pyridine | |
| 1.43 | 2-(3'-Phenylpropylthio)-5-isothiocyano-pyridine | $n_D^{25}$ 1,668 |
| 1.44 | 2-(6'-Phenylhexylthio)-5-isothiocyano-pyridine | $n_D^{25}$ 1,641 |

The following isothiocyanopyridines of formula (Ib) can be prepared in the same manner as that described in Example 7:

The following isothiocyanopyridines of formula (Ic) can be prepared in the same manner as that described in Example 8:

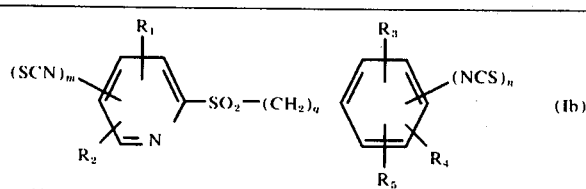

(Ib)

| Comp. No. | Compound | Physical data |
|---|---|---|
| 2.1 | 2-(4'-Methylphenylsulfonyl)-5-isothiocyano-pyridine | M.P. 150–152° C |
| 2.2 | 2-(4'-tert.Butylphenylsulfonyl)-5-isothiocyano-pyridine | M.P. 111–113° C |
| 2.3 | 2-(4'-Chlorophenylsulphonyl)-5-isothiocyano-pyridine | M.P. 163–165° C |
| 2.4 | 2-Benzylsulfonyl-5-isothiocyano-pyridine | M.P. 141–143° C |
| 2.5 | 2-(4'-Fluorobenzylsulfonyl)-5-isothiocyano-pyridine | M.P. 165–167° C |
| 2.6 | 2-(4'-Chlorobenzylsulfonyl)-5-isothiocyano-pyridine | M.P. 171–173° C |
| 2.7 | 2-(4'-Bromophenylsulfonyl)-5-isothiocyano-pyridine | M.P. 179–181° C |
| 2.8 | 2-(2',4'-Dichlorobenzylsulfonyl)-5-isothiocyano-pyridine | M.P. 140–142° C |

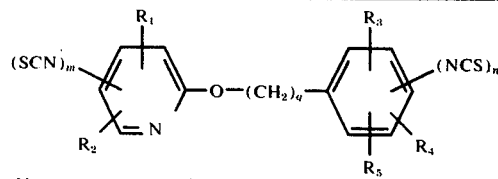

Ic

| Comp. No. | Compound | Physical data |
|---|---|---|
| 3.1 | 2-Phenoxy-5-isothiocyano-pyridine | M.P. 42–43° C |
| 3.2 | 2-Phenoxy-3-isothiocyano-pyridine | M.P. 71,5–73° C |
| 3.3 | 4-(4'-Isothiocyanophenoxy-pyridine | M.P. 51–53° C |
| 3.4 | 2-(4'-Methylphenoxy-5-isothiocyano-pyridine | M.P. 63–65° C |
| 3.5 | 2-(4'-Isothiocyanophenoxy)-4-methyl-pyridine | |
| 3.6 | 2-(3'-Methoxyphenoxy)-5-isothiocyano-pyridine | M.P. 57–59° C |
| 3.7 | 2-(4'-Methoxyphenoxy)-5-isothiocyano-pyridine | M.P. 66–68° C |
| 3.8 | 2-(2'-Methoxyphenoxy)-5-isothiocyano-pyridine | M.P. 51–53° C |
| 3.9 | 2-(4'-Methoxyphenoxy)-3-isothiocyano-pyridine | M.P. 80–82° |
| 3.10 | 2-(3'-Methoxyphenoxy)-3- | |

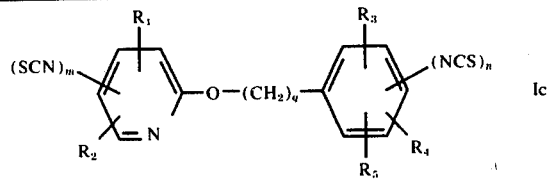

| Comp. No. | Compound | Physical data |
|---|---|---|
| | isothiocyano-pyridine | M.P. 53–55° C |
| 3.11 | 2-(4'-Ethylphenoxy)-5-isothiocyano-pyridine | $n_D^{25}$ 1.648 |
| 3.12 | 2-(3'-Trifluoromethylphenoxy)-3-isothiocyano-pyridine | M.P. 64–66° C |
| 3.13 | 2-(3'-Trifluoromethylphenoxy)-5-isothiocyano-pyridine | $n_D^{25}$ 1.605 |
| 3.14 | 2-(4'-Fluorophenoxy)-5-isothiocyano-pyridine | M.P. 83–85° C |
| 3.15 | 2-(4'-Isothiocyanophenoxy)-6-chloropyridine | |
| 3.16 | 2-(4'-Chlorophenoxy)-5-isothiocyano-pyridine | M.P. 62–64° C |
| 3.17 | 2-(3'-Chlorophenoxy)-5-isothiocyano-pyridine | $n_D^{25}$ 1.678 |
| 3.18 | 2-(4'-Isothiocyanophenoxy)-5-nitro-pyridine | M.P. 125–127° C |
| 3.19 | 2-(4'-Isothiocyanophenoxy)-6-diethylamino-pyridine | |
| 3.20 | 2-(4'-Diethylaminophenoxy)-5-isothiocyano-pyridine | |
| 3.21 | 2-(4'-Acetamidophenoxy)-5-isothiocyano-pyridine | M.P. 123–125° C |
| 3.22 | 2-(2',4'-Dimethylphenoxy)-5-isothiocyano-pyridine | $n_D^{25}$ 1.670 |
| 3.23 | 2-(2',4'-Dichlorophenoxy)-5-isothiocyano-pyridine | M.P. 51–53° C |
| 3.24 | 2-(2'-Methoxy-4'-methylphenoxy)-5-isothiocyano-pyridine | M.P. 57–58° C |
| 3.25 | 2-(2',6'-Dichloro-4'-isothiocyanophenoxy)-pyridine | |
| 3.26 | 2-(3',4',5'-Trichlorophenoxy)-5-isothiocyano-pyridine | M.P. 127–129° C |
| 3.27 | 2-Benzyloxy-5-isothiocyano-pyridine | M.P. 76–78° C |
| 3.28 | 2-(4'-Isothiocyanobenzyloxy)-pyridine | M.P. 110–112° C |
| 3.29 | 2-(4'-Fluorobenzyloxy)-5-isothiocyano-pyridine | M.P. 118–120° C |
| 3.30 | 2-(4'-Fluorobenzyloxy)-3-isothiocyano-pyridine | |
| 3.31 | 3-Isothiocyano-4-(4'-Fluorobenzyloxy)-pyridine | |
| 3.32 | 2-(2'-Fluorobenzyloxy)-5-isothiocyano-pyridine | M.P. 54–56° C |
| 3.33 | 2-(4'-Chlorobenzyloxy)-5-isothiocyano-pyridine | M.P. 133–135° C |
| 3.34 | 2(4'-Bromobenzyloxy)-5-isothiocyano-pyridine | M.P. 146–148° C |
| 3.35 | 2-(4'-Methylbenzyloxy)-5-isothiocyano-pyridine | M.P. 95–98° C |
| 3.36 | 2-(2'-Phenylethoxy)-5-isothiocyano-pyridine | M.P. 110–114° C |
| 3.37 | 2-(3'-Phenylpropoxy)-5-isothiocyano-pyridine | M.P. 72–76° C |
| 3.38 | 2-Benzyloxy-5-isothiocyano-6-methoxy-pyridine | |
| 3.39 | 2-Benzyloxy-5-isothiocyano-6-diethylamino-pyridine | |

In the same manner as that described in Example 9, there can be prepared the following isothiocyanopyridines of the general formula I d, from which corresponding acid addition salts are obtainable:

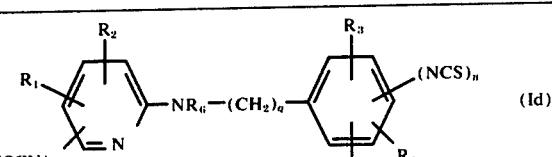

| Comp. No. | Compound | Physical data |
|---|---|---|
| 4.1 | 2-Anilino-5-isothiocyano-pyridine | M.P. 108–111° C |

-continued

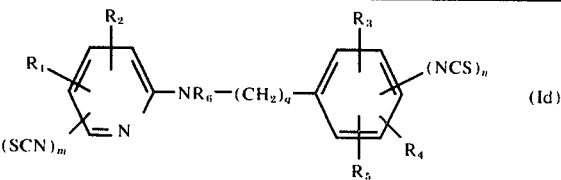

(Id)

| Comp. No. | Compound | Physical data |
|---|---|---|
| 4.2 | 2-(4'-Fluoroanilino)-5-isothio-cyano-pyridine | M.P. 150–154° C |
| 4.3 | 2-(4'-Chloroanilino)-5-isothio-cyano-pyridine | M.P. 118–121° C |
| 4.4 | 2-(4'-Bromoanilino)-5-isothiocyano-pyridine | M.P. 110–113° C |
| 4.5 | 2-(4'-Iodoanilino)-5-isothiocyano-pyridine | |
| 4.6 | 2-(4'-Methylanilino)-5-isothio-cyano-pyridine | M.P. 136–138° C |
| 4.7 | 2-(2',4'-Difluoroanilino-5-isothio-cyano-pyridine | |
| 4.8 | 2-(3',4'-Dichloroanilino)-5-isothio-cyano-pyridine | |
| 4.9 | 2-(4'-Trifluoromethylanilino)-5-iso-thiocyano-pyridine | |
| 4.10 | 2-(3'-Trifluoromethylanilino)-5-iso-thiocyano-pyridine | |
| 4.11 | 2-(4'-Ethoxyanilino)-5-isothio-cyano-pyridine | M.P. 135–136° C |
| 4.12 | 2-(4'-Butoxyanilino)-5-isothio-cyano-pyridine | M.P. 104–107° C |
| 4.13 | 2-(4'-Cyanoanilino)-5-isothio-cyano-pyridine | |
| 4.14 | 2-(4'-Hydroxyanilino)-5-iso-thiocyano-pyridine | M.P. 110–112° C |
| 4.15 | 2-(4'-Dimethylaminoanilino)-5-isothiocyano-pyridine | M.P. 149–150° C |
| 4.16 | 2-(4'-Methoxycarbonylamino-anilino)-5-isothiocyano-pyridine | |
| 4.17 | 2-(4'-Allyloxycarbonylamino-anilino)-5-isothiocyano-pyridine | |
| 4.18 | 2-[N-(4'-Fluorobenzyl)-amino]-5-isothiocyano-pyridine | |
| 4.19 | 2-[N-(4'-Chlorobenzyl)-amino]-5-isothiocyano-pyridine | M.P. 132–133° C |
| 4.20 | 2-[N-(2'-Chlorobenzyl)-amino]-5-isothiocyano-pyridine | M.P. 82–85° C |
| 4.21 | 2-[N-(4'-Bromobenzyl)-amino]-5-isothiocyano-pyridine | |
| 4.22 | 2-(N-Benzylamino)-5-isothio-cyano-pyridine | |
| 4.23 | 2-[N-(2'-Phenylethyl)-amino]-5-isothiocyano-pyridine | |
| 4.24 | 2-[N-(3',4'-Dimethylbenzyl)-amino]-5-isothiocyano-pyridine | |
| 4.25 | 2-(4'-Phenoxyanilino)-5-isothio-cyano-pyridine | M.P. 102–104° C |
| 4.26 | 2-(4'-Phenylanilino)-5-isothio-cyano-pyridine | M.P. 175–179° C |
| 4.27 | 2-(4'-Isothiocyanoanilino)-5-nitro-pyridine | M.P. 179–181° C |
| 4.28 | 2-(4'-Isothiocyanoanilino)-3-nitro-pyridine | |
| 4.29 | 2-(4-Isothiocyanoanilino)-6-chlor-pyridine | |
| 4.30 | 2-(4'-Methyl-N-acetylanilino)-5-isothiocyano-pyridine | |
| 4.31 | 2-(3'-Isothiocyanoanilino)-5-5-nitro-pyridine | |
| 4.32 | 2-(4'-Isothiocyanoanilino)-pyridine | |
| 4.33 | 4-(4'-Isothiocyanoanilino)-pyridine | |
| 4.34 | 2-(3'-Isothiocyanoanilino)-pyridine | |
| 4.35 | 2-(4'-Acetylaminoanilino)-5-isothiocyano-pyridine | |
| 4.36 | 2-(4'-Methylanilino)-5-iso-thiocyano-6-methoxy-pyridine | |
| 4.37 | 2-[N-(4'-Chlorobenzyl)-amino]-5-isothiocyano-6-methoxy-pyridine | |
| 4.38 | 2-(4'-Isothiocyanoanilino)-4-methyl-pyridine | |
| 4.39 | 2-(4'-Methylanilino)-5-iso-thiocyano-6-diethylamino-pyridine | |
| 4.40 | 2-(4'-Methoxyanilino)-5-iso- | |

-continued $$R_1 \underset{(SCN)_m}{\overset{R_2}{\diagup\hspace{-0.3em}\diagdown}} -NR_6-(CH_2)_q- \underset{R_5}{\overset{R_3}{\diagup\hspace{-0.3em}\diagdown}} (NCS)_n \quad (Id)$$

| Comp. No. | Compound | Physical data |
|---|---|---|
| | thiocyano-pyridine | M.P. 137–139° C |

Tests on mice infested by *Hymenolepis nana*

The active substances in the form of a suspension were administered by stomach probe to white mice infested with *Hymenolepis nana*. Five animals were used for each test. The active substances were administered to each animal once daily on three successive days. On the eighth day after commencement of the treatment, the animals were killed and dissected.

After dissection of the test animals, an evaluation was made on the basis of the number of tapeworms present in the intestines. Untreated mice which had been simultaneously and identically infested served as a control.

The agents were tolerated asymtomatically by the mice.

Tests on mice infested by mouse threadworms (*oxyuris*)

The active substances were administered in the form of a suspension by means of a stomach probe to white mice infested with mouse threadworms. Five animals were used for each test. The active substances were administered to each animal once daily during 3 successive days. The animals were then killed on the eighth day after commencement of the treatment and dissected.

After dissection of the test animals, an evaluation was made on the basis of the count of mouse threadworms present in the intestines. Untreated mice that had been identically infested served as a control The agents were tolerated asymtomatically by the mice.

Tests on mice infested by *Nematospiroides dubius*

The active substances in the form of a suspension were administered by stomach probe to white mice infested with *Nematospiroides dubius*. Five animals were used for each test. The active substances were administered to each animal once daily on 3 successive days. On the eighth day after commencement of the treatment, the animals were killed and dissected.

After dissection of the test animals, an evaluation was made on the basis of the count of nematodes present in the intestines. Untreated mice which had been simultaneously and identically infested served as a control.

The agents were tolerated asymtomatically by the mice.

Determination of the anthelmintic action on fowl infested with *Ascaridia galli*

One- to three-day old chickens were infested with eggs of Ascaridia galli (ascarides). A group of five chickens was used for each test. Four to five weeks after infestation, the active substances were administered to the chickens in the form of one daily dose on 3 successive days. Infested but untreated birds served as a control.

The number of *Ascaridia galli* excreted by each test group in the course of 5 days after the first administration was determined daily, and the number of worms still present in the intestines following dissection on the fifth day of the test likewise counted. The number of chickens free from worms was also determined.

Tests on rats infested by *Fasciola hepatica*

White laboratory rats were infested with common liver flukes (*Fasciola hepatica*). After expiration of the prepatent period, the infestation of the rats by common liver flukes was determined by means of three independent excrement analyses.

In each test, two infested rats were treated in each case with the active substance, administered in the form of a suspension by stomach probe, once daily on three successive days. An excrement analysis to determine the content of common liver fluke eggs was made once weekly in the third, fourth and fifth week after administration of the active substance. At the end of the fifth week after commencement of the test, the test animals were killed and examined to determine whether liver flukes were still present.

The effectiveness of the isothiocyanopyridines according to the invention as defoliating and desiccating agents is illlustrated by the following tests.

The active substances are applied, either (a) as a 0.5% aqueous suspension (obtained from a 25% emulsion concentrate) or (b) as a 10% powder concentrate, to ca. 20 cm high cotton plants, shortly before the appearance of the third leaf. In each case, it is only the surface and the stem of the leaf of the cotyledons which are treated. The plants are then stored in a greenhouse at 24° to 26° and with 45 to 60% relative humidity. The test is evaluated after 10 days.

The following examples describe the methods of producing the preparations of active substances suitable as anthelmintic agents and as feed additives. Parts are expressed as parts by weight.

---

Coated granulate
Composition:
25.0 parts of an active compound of formula I,
45.0 parts of microcrystalline cellulose,
2.5 parts of highly dispersed silicic acid,
7.5 parts of talcum, und
20.0 parts of polyvinyl acetate.

---

The active substance, talcum and ca. 90% of the amount of silicic acid are successively worked into the solution of polyvinyl acetate in acetone/ethyl acetate mixture (1:1), and the whole mixed with the prepared portion of microcrystalline cellulose in a planetary mixer. The remainder of the silicic acid is subsequently added to the mixture, and this then kneaded until ready for granulation. The mixture is transferred to an oscillator-granulator and granulated to the desired particle size. The resulting granulate is dried and again granulated in a granulator down to a particle size of 30–300 μ.

Dispersible powder

The following constituents are used in the preparation of 50% dispersible powders:

| a) | 50 | parts of an active substance according to the invention, |
| --- | --- | --- |
| | 1 | part of a polyethyleneoxypropylene glycol having a molecular weight of ca. 2000 (Pluronic L 61), |
| | 5 | parts of the ammonium salt of a sulphonated naphthalene sulphonic acid/phenol/formaldehyde condensate (Irgatan AG1), |
| | 44 | parts of kaolin; |
| b) | 50 | parts of an active substance according to the invention, |
| | 1 | part of a polyethyleneoxypropylene glycol having a molecular weight of ca. 8000 (Pluronic F 68), |
| | 0.5 | part of sodium lignin sulphonate, |
| | 48.5 | parts of sodium silicate. |

The active substances are mixed with the carriers and distributing agents and finely ground. The resulting powder can be mixed with liquid or pasty feeding stuffs and thus administered to domestic and farm animals.

Paste

The following substances are used in the preparation of a 40% paste:

| 40.0 | parts of an active substance according to the invention, |
| --- | --- |
| 2.5 | parts of sodium lignin sulphonate, |
| 0.3 | part of sodium benzoate, |
| 10.0 | parts of polyoxyethylenealkyl ether, |
| 47.2 | parts of distilled water. |

The active substance and the distributing agents are intimately mixed. The paste thus obtained is mixed with liquid and pasty feeding stuffs for administration to domestic and to farm animals.

Feed additive press cakes

The following substances are used in the preparation of 35% feed additive press cakes:

| 35 | parts of an active substance according to the invention, |
| --- | --- |
| 15 | parts of molasses, |
| 5 | parts of licorice powder, |
| 25 | parts of dried green meal, |
| 20 | parts of ground bran. |

The active substance and the distributing agents are mixed and formed into press cakes in an animal-feed-press. The feed additive concentrate obtained is mixed with the feed and thus administered to domestic and farm animals.

Emulsifiable concentrate

An emulsifiable concentrate is obtained by mixing together the following substances:

| 2 | parts of an active substance according to the invention, |
| --- | --- |
| 2 | parts of a polyethyleneoxypropylene glycol having a molecular weight of ca. 3000 (Pluronic L 64), and |
| 96 | parts of acetone. |

The concentrate obtained can be diluted with water to give emulsions of any desired concentration, and administered, e.g. as drink, to domestic and farm animals.

Oily formulation

| 40 | parts of active substance according to the invention are ground as finely as possible in a suitable mill, and then homogeneously mixed, e.g. on a roll mill, with |
| --- | --- |
| 60 | parts of arachis oil (peanut oil). |

These oily pastes can be administered orally to the animals.

We claim:

1. A compound of the formula

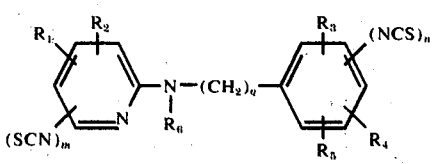

wherein
R₁ is hydrogen,
R₂ is hydrogen,
R₃ is hydrogen, halogen, methyl, methoxy, ethoxy, butoxy, hydroxy, dimethylamino, phenoxy, or phenyl,
R₄ and R₅ are hydrogen,
R₆ is hydrogen,
m is 1,
n is 0,
q is 0 or 1.

2. The compound of claim 1, wherein said compound is 2-(4'-fluoroanilino)-5-isothiocyano-pyridine.

3. The compound of claim 1, wherein said compound is 2-(4'-chloroanilino)-5-isothiocyano-pyridine.

4. The compound of claim 1, wherein said compound is 2-(4'-bromoanilino)-5-isothiocyano-pyridine.

5. The compound of claim 1, wherein said compound is 2-(4'-methylanilino)-5-isothiocyano-pyridine.

* * * * *